(12) United States Patent  (10) Patent No.: US 8,185,407 B2
Brimdyr  (45) Date of Patent: May 22, 2012

(54) REFERRAL REQUEST SYSTEM

(75) Inventor: Joshua Logan Howard Brimdyr, Dennisport, MA (US)

(73) Assignee: Medunity Inc., East Sandwich, MA (US)

( * ) Notice: Subject to any disclaimer, the term of this patent is extended or adjusted under 35 U.S.C. 154(b) by 2779 days.

(21) Appl. No.: 10/924,504

(22) Filed: Aug. 24, 2004

(65) Prior Publication Data

US 2006/0047537 A1   Mar. 2, 2006

(51) Int. Cl.
*G06Q 10/00* (2012.01)
*G06Q 50/00* (2012.01)

(52) U.S. Cl. ............................................ 705/2; 705/3
(58) Field of Classification Search .............. 705/2–3; 707/500
See application file for complete search history.

(56) References Cited

U.S. PATENT DOCUMENTS

| | | | |
|---|---|---|---|
| 2002/0026329 A1* | 2/2002 | Saito et al. | 705/3 |
| 2002/0065682 A1* | 5/2002 | Goldenberg | 705/2 |
| 2002/0161795 A1* | 10/2002 | O'Rourke | 707/500 |
| 2004/0044546 A1* | 3/2004 | Moore | 705/2 |

OTHER PUBLICATIONS

'Practice Management PLUS System'. American Medical Software [online]. 1997-2005 [retrieved on Apr. 25, 2005]. Retrieved for the Internet:<URL: http://www.americanmedical.com/Products.htm>.
'NDC Medisoft'. Medisoft Patient Accounting Software [online]. 2005 [retrieved on Apr. 25, 2005]. Retrieved from the Internet:<URL: http://www.ambanet.net/medisoft.htm>.

* cited by examiner

*Primary Examiner* — Robert Morgan
*Assistant Examiner* — Joseph Burgess

(57) ABSTRACT

A method for electronically managing patient referrals includes, in a network of interconnected computers, submitting a referral request by a first provider, accepting the referral request by a second provider, obtaining an insurance approval of the referral request, importing a medical record for a patient from a external system, exporting the imported medical record to the external system, updating the medical record with diagnostic information, and updating a status of the referral request.

57 Claims, 7 Drawing Sheets

REFERRAL REQUEST SYSTEM

TECHNICAL FIELD

This invention relates to web applications, and more particularly to a referral request system.

BACKGROUND

In the United States, medical insurance plans operate under a gatekeeper concept. This is a system under which a member must select a primary care physician (PCP) who then provides or authorizes all care for that particular member. Any member needing to see a specialist provider, such as a cardiologist or dermatologist, must first obtain a medical referral from the PCP. A failure to comply with this requirement generally results in a denial of coverage for the specialist visit. In most instances, the member (hereinafter referred to as the "patient") cannot schedule an appointment with the specialist without an authorized and approved referral request.

The PCP is usually a general practitioner, and she is responsible for determining whether the patient requires the specialist. As a result, the PCP must either perform her own office examination of the patient, or at least review the patient's medical records before issuing the referral request. The PCP then sends a referral request to the patient's insurance company for approval. If the insurance company approves the referral request, then the PCP mails this approved referral request to the specialist's office. All of the above transactions must transpire before the patient can schedule an appointment with the specialist. A significant lapse in time can exist between the patient's initial need and when the patient actually visits the specialist.

The passage of the Health Insurance Portability and Accountability Act (HIPAA) by Congress in 1996 has further complicated the referral request system. HIPAA establishes rigorous standards for protecting sensitive patient information. Health care providers are legally liable for maintaining these strict standards. As a result, many medical offices no longer fax or e-mail referral requests. Instead, they mail hard-copies of the referrals to the recipient offices, and then confirm receipt with telephone calls. Aside from generating a tremendous amount of paperwork, such transactions also contribute to loss of time, decrease in efficiency and productivity, and increased financial burdens on health care providers. Moreover, constant mailing of documents between the various offices invariably results in information that is lost in transaction.

In addition, the initial referral request does not provide unlimited visits to the specialist. If the patient requires additional visits to the specialist which are not listed in the original referral request, she must submit a new treatment plan to her PCP. Thus, the patient bears the burden of continually inquiring about the status of her referral (e.g. whether the time frame has expired or number of visits been exceeded) whenever she schedules another appointment with the specialist office.

SUMMARY

The present invention provides methods and apparatus, including computer program products, for electronic patient referral.

In a general aspect, the application is directed to a method which includes in a network of interconnected computers, submitting an referral request by a first provider, accepting the referral request by a second provider, obtaining an insurance approval of the referral request, importing a medical record for a patient from a external system, exporting the imported medical record to the external system, updating the medical record with diagnostic information, and updating a status of the referral request.

Another aspect is a computer program product which is tangibly embodied in an information carrier. The computer program product is operable to cause a data processing apparatus, in a network of interconnected computers, to submit an referral request by a first provider, accept the referral request by a second provider, obtain an insurance approval of the referral request, import a medical record for a patient from a external system, export the imported medical record to the external system, update the medical record with diagnostic information, and update a status of the referral request.

Yet another aspect is an apparatus which includes in a network of interconnected computers, means for submitting a referral request from a first provider. The apparatus also includes means for accepting the referral request by a second provider, means for obtaining an insurance approval corresponding to the referral request, means for importing a medical record for a patient from an external system and exporting to the external system, means for receiving a diagnostic information from the second provider, and means for updating a status of the referral request. The diagnostic information is used to update the medical record.

Any of the above aspects may include one or more of the following features. In one implementation, the network of interconnected computers comprises a server system. The server system stores a referral request form and a referral data form corresponding to the referral request form.

In another implementation, the first provider includes a health care provider. Another implementation has the first provider including the patient submitting the referral request to the first provider or the second provider. In yet another implementation, the second provider includes a health care provider.

One implementation accepts the referral request by further including monitoring the network by the second provider, submitting an acknowledgment of the referral request, placing the patient on a wait-list, providing an appointment for the patient, and examining the patient by the second provider.

In yet another implementation, the medical record includes medical history information for the patient. The medical history information includes personal medical information, family information, and social information. One implementation imports and exports the medical record by entering the medical history information manually. Another implementation imports and exports the medical record by hyperlinking the medical history information to the external system. Still another implementation imports and exports using an application programming interface (API). Yet another implementation imports and exports the medical record by using a paste and post method. The paste and post method includes selecting the medical history information from an external system, copying the medical history information, pasting the medical history information into a clipboard, matching the medical history information to a plurality of fields within the external system, and filling a number of fields with corresponding medical history information.

An implementation includes within the diagnostic information a summary report of an office examination of the patient, patient laboratory test results, and a list of medication prescribed by the second provider. Another implementation returns the updated referral request to the first provider.

In one implementation, the first provider or second provider performs an update of the status of the referral request.

The status of the referral request includes an indication of whether the patient has been seen by the second provider. In addition, the status is filtered and sorted according to a category.

The details of one or more features of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
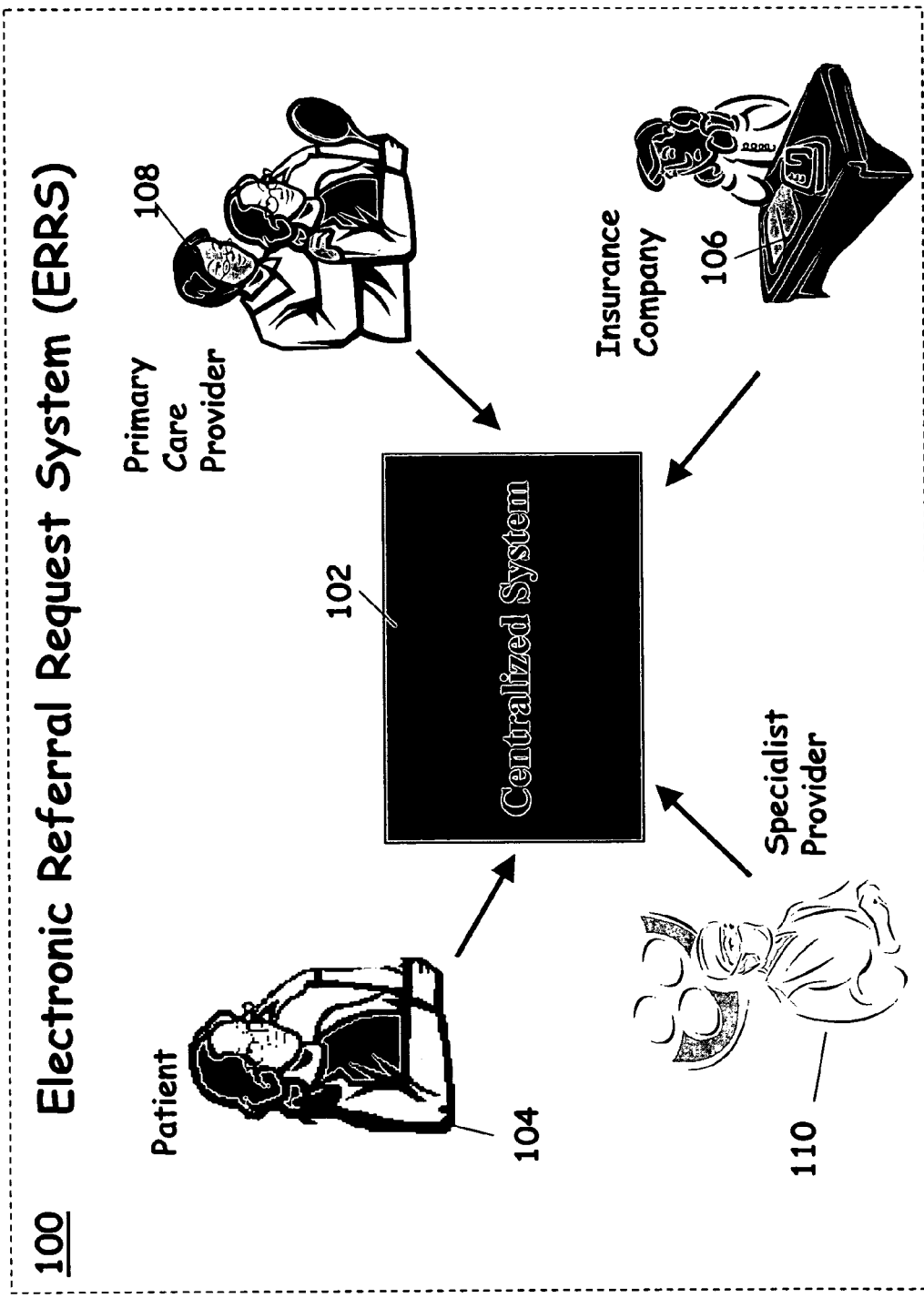
FIG. 1 shows the general process for obtaining a referral request using the Referral Request System (ERRS).

As shown in FIG. 1, Electronic Referral Request System (ERRS) 100 manages a network of activities that occur for obtaining a medical referral. Using centralized system 102, ERRS 100 allows for direct and paperless interactions between patients 104, insurance companies 106, and health care providers, such as PCPs 108 and specialists 110. ERRS 100 advantageously eliminates telephone, facsimile, electronic mail, and postal mail interactions between the parties. Thus, ERRS 100 facilitates a seamless and more efficient process for obtaining a medical referral.

ERRS 100 can be implemented as a client server network, or server system. Client/server describes a relationship between two computer programs in which one program, the client, makes a service request from another program, the server, which fulfills the request. Although the client/server idea can be used by programs within a single computer, it is a more important idea in a network. In a network, the client/server model provides a convenient way to interconnect programs that are distributed efficiently across different locations.

In the client/server model, one server, sometimes called a daemon, is activated and awaits client requests. Typically, multiple client programs share the services of a common server program. Both client programs and server programs are often part of a larger program or application. Relative to the Internet, a Web browser is a client program that requests services from a Web server in another computer somewhere on the Internet.

Figure 2:
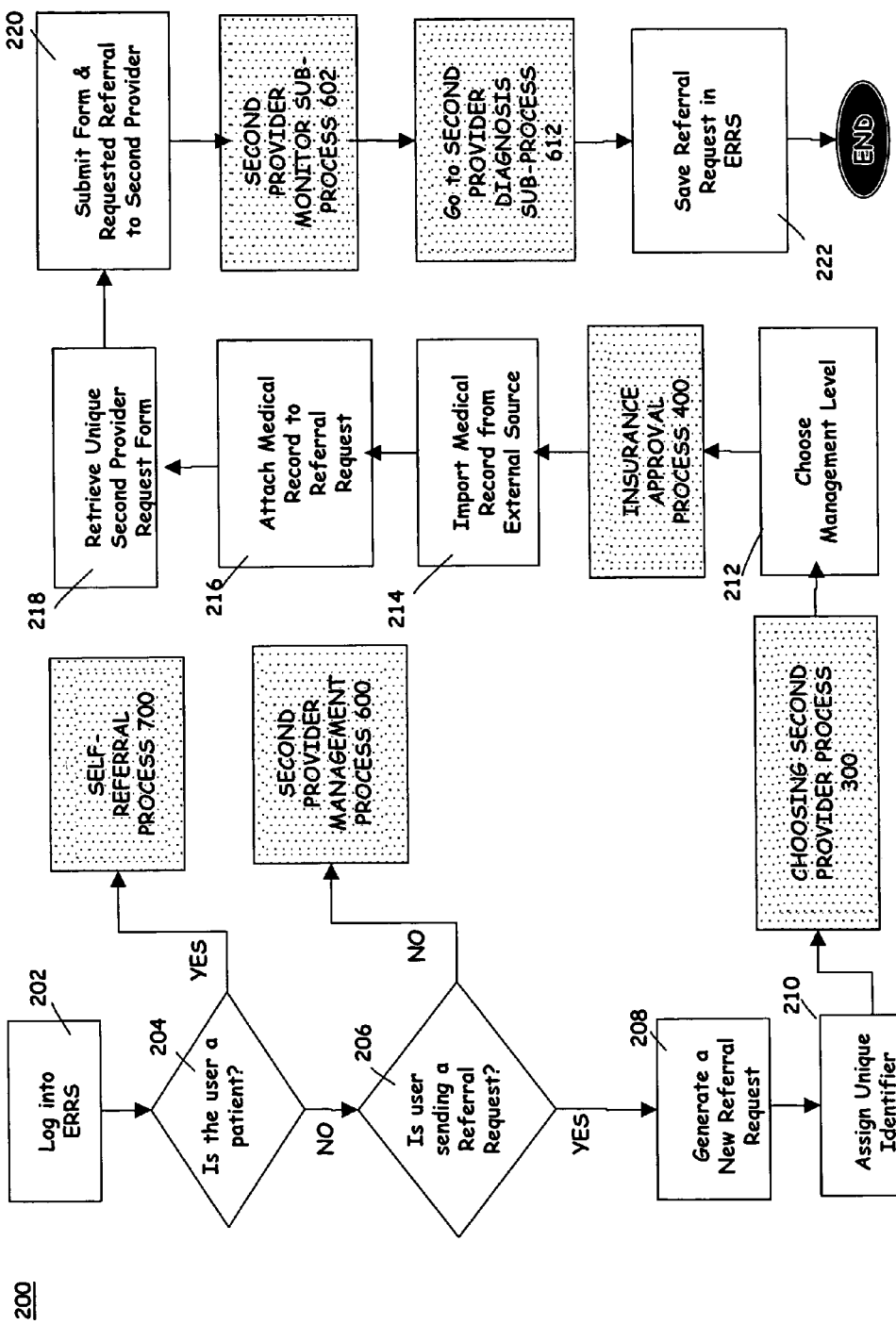
FIG. 2 is a flow diagram of a process for managing the entire referral request process.

FIG. 2 illustrates process 200 which manages a referral request process for patient 104. Process 200 logs (202) a user into ERRS 100 and inquires (204) whether the user is patient 104. The user who is patient 104 initiates process 700, which permits patient 104 to generate the referral request by herself using ERRS 100, as described below.

For the user who is not a patient 104, process 200 inquires (206) whether the user is sending the referral request. If the user is not sending, but instead is receiving the referral request, then process 200 labels this user as a "second provider." A user who is the second provider is forwarded to process 600, which illustrates the management of ERRS 100 by the second provider. Generally, the second provider is specialist provider 110, or in other words, a physician who renders care in a specific field of medicine, such as cardiology or dermatology. However, in other implementations, the second provider also can be PCP 108.

Users who are sending the referral request are labeled "first providers." For the first providers, process 200 generates (208) a new referral request for patient 104. Every time patient 104 needs to see the second provider, a new referral request is generated (208). The new referral request details basic demographic information about patient 104, such as name, date of birth, gender, as well as the first provider's notes and evaluation of patient 104. The first provider can be either PCP 108 or specialist 110. In addition, patient 104 may also send the referral request, as described below in process 700.

As shown in FIG. 2, after generating (208) the new referral request, process 200 assigns (210) an unique identifier to the referral request. The unique identifier helps ERRS 100 track the new referral request, as well as, distinguish the new request from other requests which are associated with patient 104. Process 200 then selects a second provider using sub-process 300.

Figure 3:
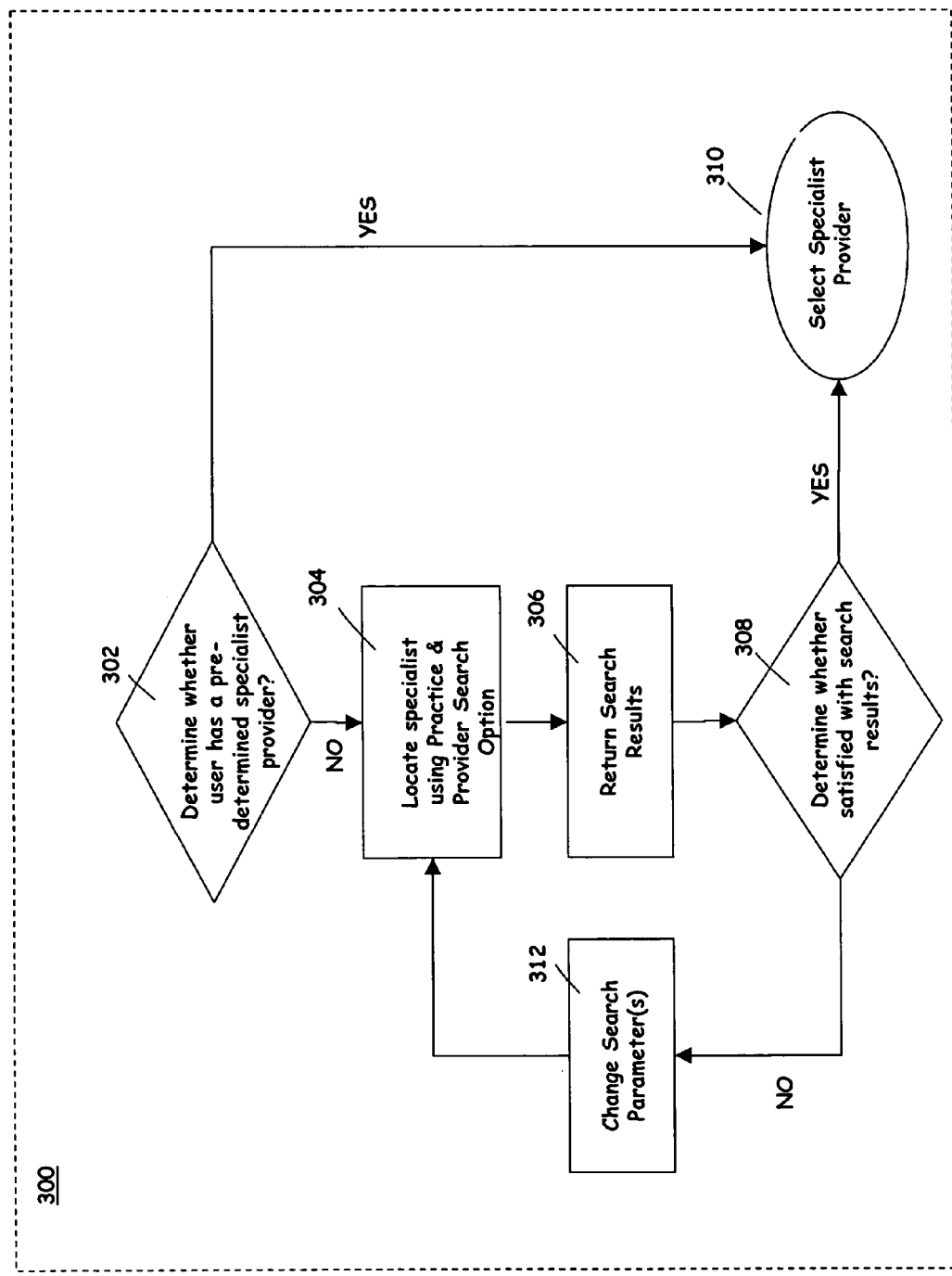
FIG. 3 is a flow diagram of a process for choosing a second provider.

FIG. 3 illustrates sub-process 300, which helps the user select an appropriate second provider. Sub-process 300 determines (302) whether the user already has a second provider that she wishes to use. For example, patient 104 may wish to see the same dermatologist as her mother. In another example, PCP 108 may wish to recommend patient 104 to see a particular endocrinologist who specializes in women's fertility treatments. If the user already has a pre-determined specialist provider, sub-process 300 selects (310) that particular specialist 108. If the user does not have a particular specialist in mind, sub-process 300 locates (304) an appropriate provider using a Provider Search Function. The Provider Search Function contains a number of pre-defined parameters from which patient 104 may select and search for the provider. In one implementation, the pre-defined parameters include specialty type, provider name, and location of the provider's office. In other implementations, patient 104 may search for the provider according to gender, age, area of specialization, or educational background. Any number of pre-defined parameters may be used within the Provider Search Function.

After the Provider Search Function returns (306) a number of search results, the user can evaluate (308) whether she is satisfied with the findings. If the user is satisfied with the search results, she completes sub-process 300 by selecting (310) the specialist provider. However, if the user is dissatisfied with the search results, she may choose to repeat the Provider Search Function by changing (312) one or more of the search parameters and locating (304) another set of providers.

Referring back to FIG. 2, selection of the second provider prompts process 200 to choose (212) the management level for the referral request. In one implementation, the user may choose (212) to manage the referral request exclusively, thus prohibiting any other providers to view or manage the referral request. However, in other implementations, the user may choose (212) to co-manage, which allows other providers to modify the referral request. In some implementations, the level of management (e.g. modification permitted, modification not permitted) can be represented using binary values, such as "One" or "Zero" or "ON" or "OFF". Upon choosing (212) the management level, process 200 forwards the referral request to insurance company 106 for approval, as described in process 400.

Figure 4:
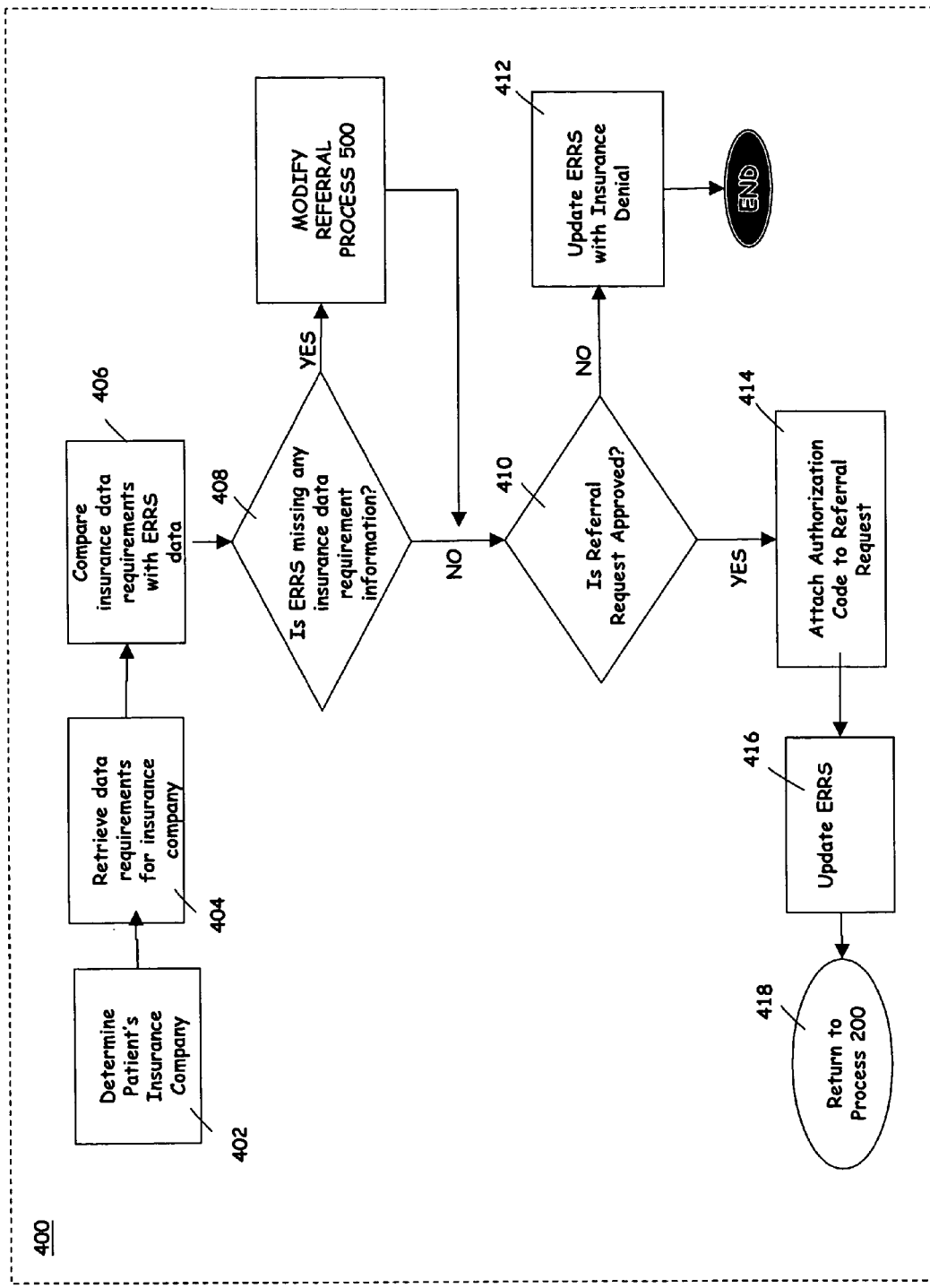
FIG. 4 is a flow diagram of a process for obtaining an insurance approval.

As shown in FIG. 4, process 400 manages the insurance approval process. Process 400 determines (402) which insurance company 106 provides coverage for patient 104, retrieves (404) the data requirements for that insurance company 106, and compares (406) the retrieved insurance data requirements with the patient information available within ERRS 100. Data requirements include all information that insurance company 106 needs in order to decide whether to authorize the referral request.

By comparing (406) the insurance data requirements against the available ERRS information, process 400 determines (408) whether any necessary information is missing. If there are missing requirements information, process 400 is forwarded to process 500.

Figure 5:
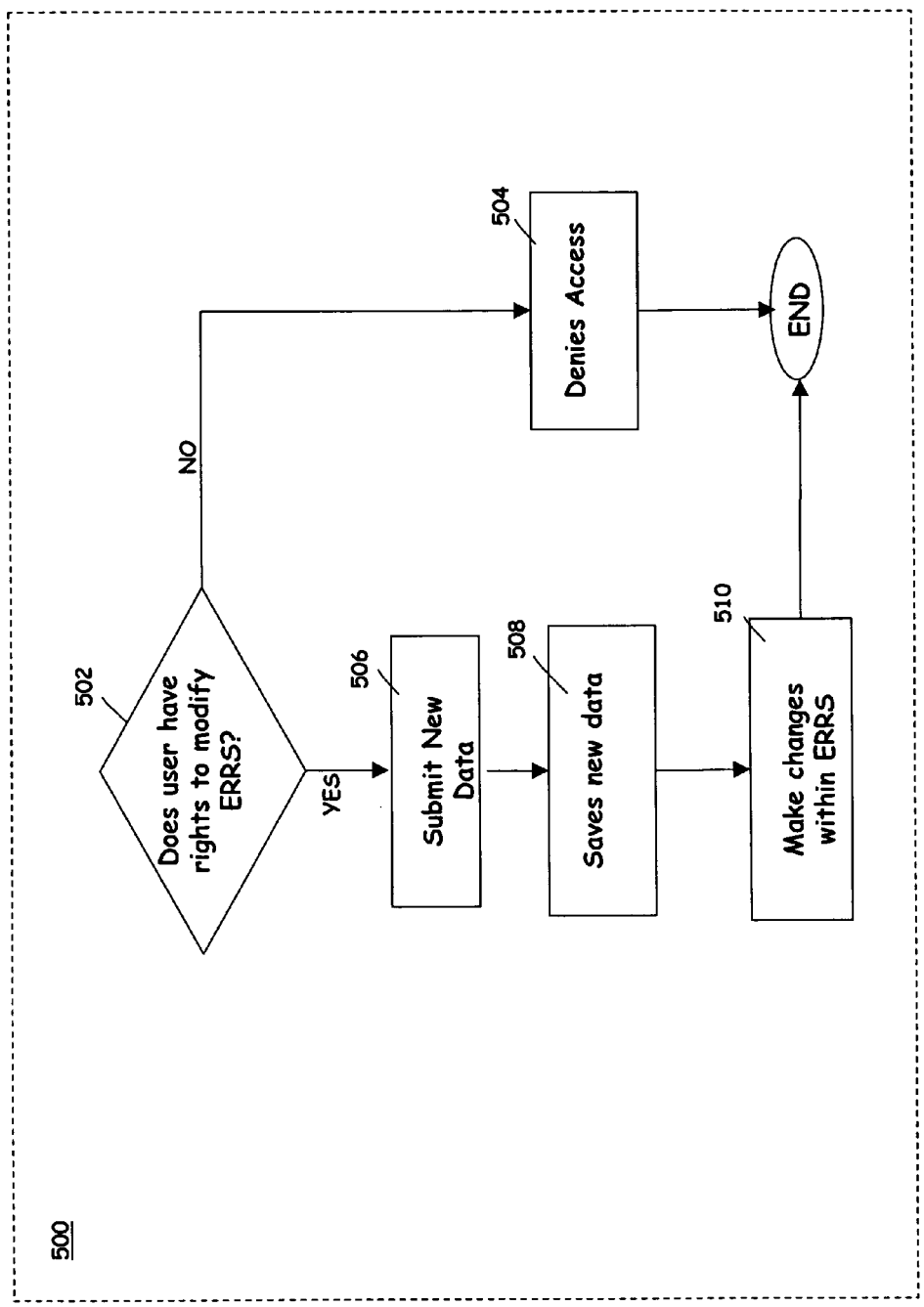
FIG. 5 is a flow diagram of a process for modifying the referral request.

As shown in FIGS. 4 and 5, process 500 modifies the information available within ERRS 100. Process 500 determines (502) whether the user has the right to modify ERRS 100. Access is denied (504) to users who do not have the proper authority. However, if the user possesses modification rights, then process 500 permits the user to submit (506) new data for modifying ERRS 100. Process 500 saves (508) the new data and makes (510) the changes within ERRS 100.

However, if ERRS 100 contains all the necessary requirements information, then process 400 determines (410) whether to authorize the referral request. If the referral request is denied, process 400 updates (412) ERRS 100 with the insurance denial. If the referral request is approved, process 400 attaches (414) an authorization code to the referral request and updates (416) ERRS 100 with the new information. The newly approved referral request is then returned (418) to process 200.

Referring back to FIG. 2, receipt of the approved referral request causes process 200 to import (214) one or more medical records for patient 104 from an external system, or third party application system. The medical record contains a complete medical history for patient 104, including a detailed review of past medical problems and all current symptoms. The past medical history can include comments regarding past illnesses and their treatment, accidents, surgeries, allergies and any prescribed medications. The medical record may also contain information about close family members and their history of illnesses and causes of death. In addition, the medical record may include the social history for patient 104, such as the use of recreational drugs and alcohol, smoking habits, sexual history, and stress levels stemming from her work and personal life.

In one implementation, importing (214) the medical record includes automatically importing the patient data information from an API (Application Programming Interface) via the external system. An API is the specific method prescribed by a computer operating system or by an application program by which a programmer writing an application program can make requests of the operating system or another application. Another implementation imports (214) the medical record by hyperlinking the patient's information into a external system. Still another implementation includes manually entering the required information into the necessary fields. Yet another implementation includes a paste and post method. The paste and post method includes selecting the patient's information from an external system, copying the information, and pasting into a clipboard. The method further includes matching the information located on the clipboard with pre-determine fields found within a medical record form, and then filling the pre-determined fields with the appropriate information. The clipboard represents a section of a computer memory that is used to temporarily hold data that has been cut or copied for transfer into another location. After importing (214) the medical record, process 200 attaches (216) the medical record to the referral request.

Process 200 retrieves (218) a referral request form that is unique to the selected second provider. This unique second provider request form is submitted (220) together with the referral request and attached medical records to the second provider. Submission (220) of these items triggers sub-process 602 which illustrates the management of ERRS 100 by the second provider.

Figure 6:
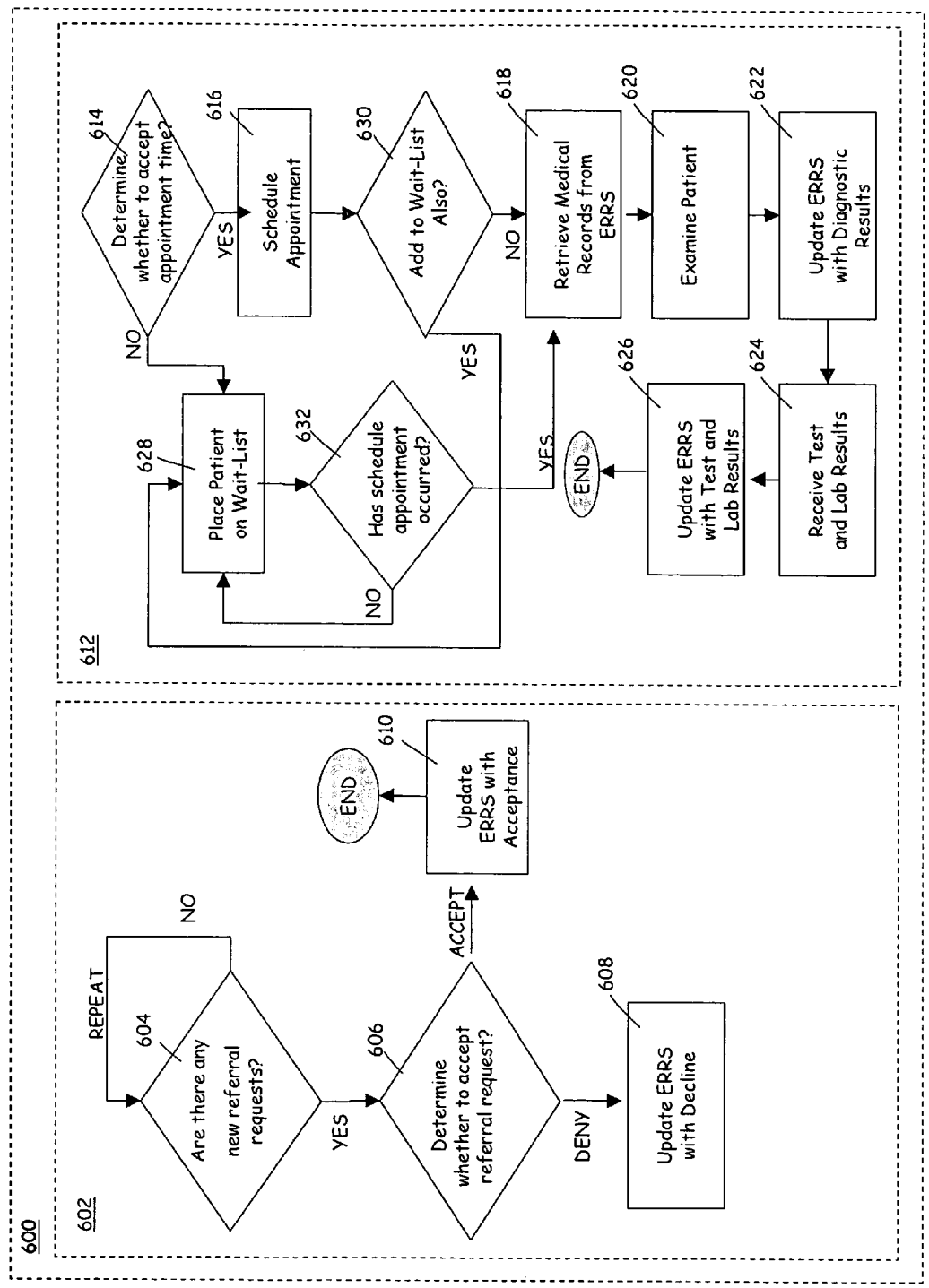
FIG. 6 is a flow diagram of a process for managing the ERRS by the second provider.

As shown in FIGS. 2 and 6, sub-process 602 repeatedly inquires (604) ERRS 100 for new referral requests until one is submitted. The second provider decides (606) whether to accept or decline the referral request. A denial of the referral request results in sub-process 602 updating (608) ERRS 100 with the denial. An acceptance of the referral request results in sub-process 602 updating (610) ERRS 100 with the acceptance. In addition, the user can specify (634) on the referral request any special instructions, such as the urgency of care.

Once the second provider accepts the referral request, sub-process 612 then performs a diagnosis on patient 104 and updates ERRS 100 with the results from that diagnosis. Sub-process 612 permits the second provider to determine (614) whether to accept the proposed appointment time. If the second provider rejects the proposed appointment time, then patient 104 is placed (628) on a wait-list. However, if the second provider accepts the appointment time, then sub-process 612 schedules (616) an appointment and queries (630) whether patient 104 also wants to be added to the wait-list in order to wait for a better time. This option of keeping the scheduled appointment, while simultaneously waiting for a better time greatly reduces the down-time that the second provider commonly experiences from last-minute cancellations.

If patient 104 elects to be on the wait-list, she remains on the wait-list until the desired appointment time becomes available. However, if the originally schedule appointment occurs (632) before the desired appointment time, or if patient 104 is pleased with her scheduled appointment time, then sub-process 612 retrieves (618) the medical records for patient 104 from ERRS 100. The second provider examines (620) patient 104 and updates (622) ERRS 100 with the diagnostic results.

Diagnostics results may include a summary of the office examination, test results conducted in the office, and any additional observations or note made by the second provider. Moreover, in some implementations, the second provider may run laboratory tests on patient 104. For example, the second provider can take a blood sample from patient 104 in order to evaluate her cholesterol and fasting-blood sugar levels. In another example, urine samples are taken from patient 104 in order to test for adult on-set diabetes, or perhaps to determine whether patient 104 is pregnant. In still another example, the second provider can remove a mole from patient 104 and perform a biopsy in order to test for cancer. Any number of laboratory tests can be conducted on patient 104.

Additionally, results from the laboratory tests can be received (624) by the second provider at a later point in time. Once the second provider receives (624) the test results, she can update (626) ERRS 100 with the new test results.

Process 200 then saves (222) the referral request within ERRS 100. In some implementations, the first provider can check the status of patient 104 on ERRS 100 in order to confirm that patient 104 actually has visited the recommended second provider. The status of patient 104 can be organized into a series of pre-determined categories from which the providers may search.

Figure 7:
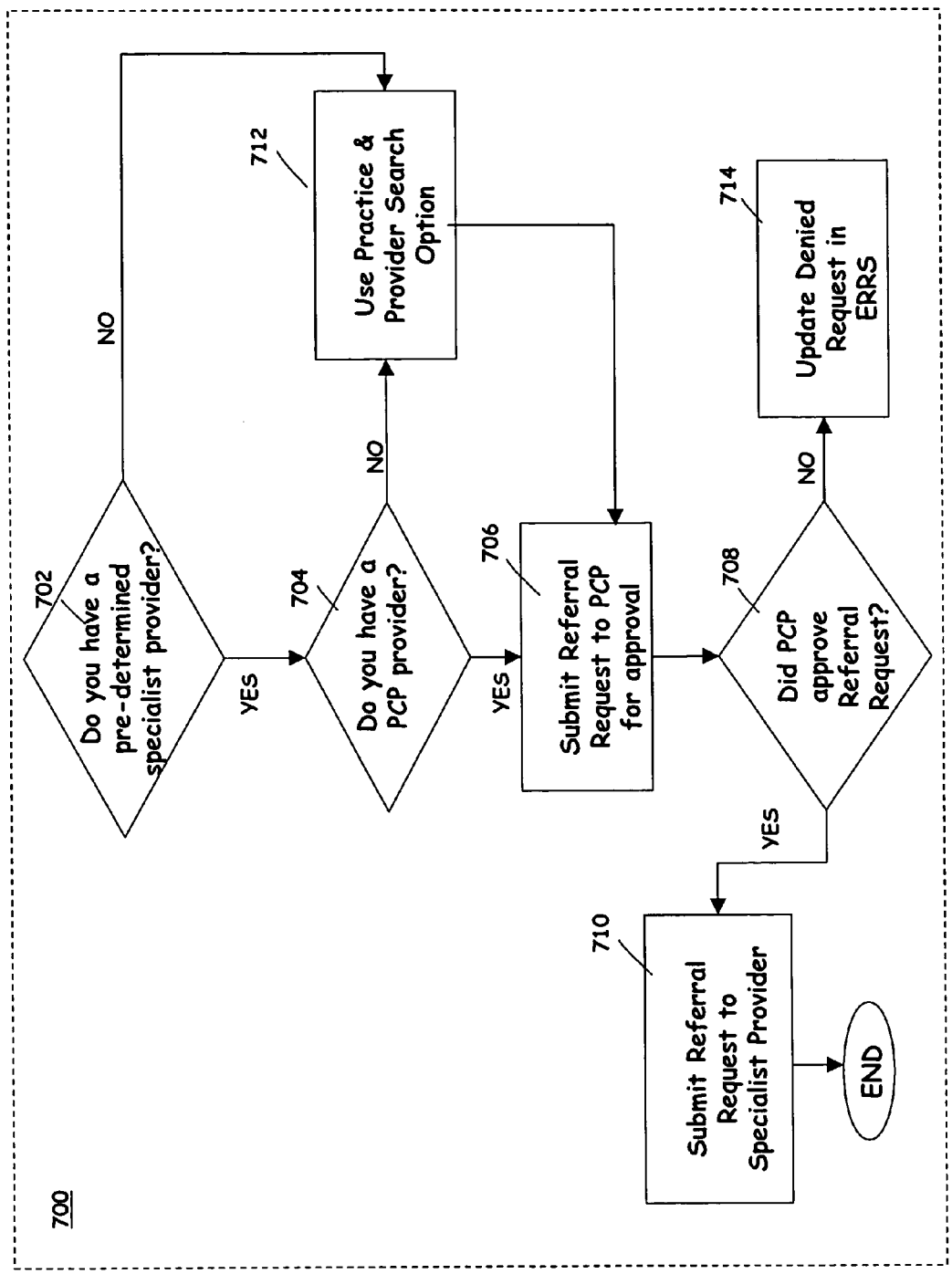
FIG. 7 is a flow diagram of a process for obtaining the referral request by a patient.

Another implementation allows patient 104 to generate her own referral request using ERRS 100, as shown in process 700 (FIG. 7). Process 700 inquires (702) whether patient 104 already has a specialist provider and determines (704) whether patient 104 has a primary care provider. Where patient 104 does not have a pre-determined specialist 110 and/or PCP 108, process 700 locates (712) a provider for patient 104 using the Provider Search Function, as described above in sub-process 300.

For patients who have a pre-determined specialist 110 and a PCP 108, process 700 submits (706) a referral request for the selected specialist to PCP 108. If PCP 108 approves (708) the requested referral, then process 700 submits (710) the referral request to the selected specialist 110. On the other hand, if PCP 108 denies the referral request, process 700 updates (714) ERRS 100 to show the denied request.

The system, described herein, is not limited to use with the hardware and software described herein; they may find applicability in any computing or processing environment and with any type of machine that is capable of running machine-readable instructions, such as a computer program.

The system may be implemented in digital electronic circuitry, or in computer hardware, firmware, software, or in combinations thereof. The system may be implemented via a computer program product, i.e., a computer program tangibly embodied in an information carrier, e.g., in a machine-readable storage device or in a propagated signal, for execution by, or to control the operation of, data processing apparatus, e.g., a programmable processor, a computer, or multiple computers. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network.

Method steps of the system can be performed by one or more programmable processors executing a computer program to perform the functions of the processes of the system. The method steps can also be performed by, and the processes can be implemented as special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. Elements of a computer include a processor for executing instructions and one or more memory devices for storing instructions and data. Generally, a computer will also include, or be operatively coupled to receive data from, or transfer data to, or both, one or more mass storage devices for storing data, e.g., magnetic, magneto-optical disks, or optical disks. Information carriers suitable for embodying computer program instructions and data include all forms of non-volatile memory, including by way of example, semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, the system can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The system can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the record extractor, or any combination of such back-end, middleware, or front-end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on respective computers and having a client-server relationship to each other.

The processes of the system are not limited to the implementations set forth herein. For example, the steps of the processes can be rearranged and/or one or more such steps can be omitted to achieve similar results. The system may link to existing business models, thereby providing enhanced flexibility. The processes may be fully automated, meaning that they operate without user intervention, or interactive, meaning that all or part of each process includes some user intervention.

The system, described herein, is not limited to the specific formats set forth above. Elements of different implementations may be combined to form another implementation not specifically set forth above. Other implementations not specifically described herein are also within the scope of the following claims.

What is claimed is:

1. A method for electronically managing patient referrals, said method comprising in a network of interconnected computers:

causing a particular computer in the network of interconnected computers to execute instructions tied to the particular computer, said instructions being instructions for submitting a referral request by a first provider;

causing a particular computer in the network of interconnected computers to execute instructions tied to the particular computer, said instructions being instructions for accepting the referral request by a second provider;

causing a particular computer in the network of interconnected computers to execute instructions tied to the particular computer, said instructions being instructions for obtaining an insurance approval of the referral request;

causing a particular computer in the network of interconnected computers to execute instructions tied to the particular computer, said instructions being instructions for importing a medical record for a patient from a external system and exporting an updated medical record to the external system;

causing a particular computer in the network of interconnected computers to execute instructions tied to the particular computer, said instructions being instructions for updating the referral request with diagnostic information; and causing a particular computer in the network of interconnected computers to execute instructions tied to the particular computer, said instructions being instructions for updating a status of the referral request.

2. The method of claim 1, wherein the network of interconnected computers comprises a server system.

3. The method of claim 2, wherein the server system stores a referral request form.

4. The method of claim 2, wherein the server system stores a referral data form corresponding to the referral request form.

5. The method of claim 1, wherein the first provider comprises a health care provider.

6. The method of claim 1, wherein the first provider comprises the patient submitting the referral request to the first provider or the second provider.

7. The method of claim 1, wherein the second provider comprises a health care provider.

8. The method of claim 1, wherein accepting the referral request further comprises:
monitoring the network by the second provider;
submitting an acknowledgment of the referral request;
placing the patient on a wait-list;
providing an appointment for the patient; and
examining the patient by the second provider.

9. The method of claim 1, wherein the medical record comprises medical history information for the patient, the medical history information comprising personal medical information, family information, and social information.

10. The method of claim 1, wherein importing and exporting the medical record comprises entering the medical history information manually.

11. The method of claim 1, wherein importing and exporting the medical record comprises hyperlinking the medical history information to the external system.

12. The method of claim 1, wherein importing and exporting the medical record comprises an application programming interface (API).

13. The method of claim 1, wherein importing and exporting the medical record comprises a paste and post method.

14. The method of claim 13, wherein the paste and post method further comprises: selecting the medical history information from an external system; copying the medical history information; pasting the medical history information into a clipboard; matching the medical history information to a plurality of fields within the external system; and filling the plurality of fields with corresponding medical history information.

15. The method of claim 1, wherein the diagnostic information comprises: a summary report of an office examination of the patient;
patient laboratory test results; and a list of medication prescribed by the second provider.

16. The method of claim 1, wherein the updated referral request is returned to the first provider.

17. The method of claim 1, wherein updating the status of the referral request is performed by the first provider or second provider.

18. The method of claim 1, wherein the status of the referral request comprises an indication of whether the patient has been seen by the second provider.

19. The method of claim 1, wherein the status is filtered and sorted according to a category.

20. A computer-readable medium having encoded thereon software for electronically managing patient referrals, said software including instructions for causing a data processing apparatus, in a network of interconnected computers, to:
submit a referral request by a first provider;
accept the referral request by a second provider;
obtain an insurance approval of the referral request;
import a medical record for a patient from a external system and export the imported medical record to the external system;
update the referral request with diagnostic information; and
update a status of the referral request.

21. The computer-readable medium of claim 20, wherein the network of interconnected computers comprises a server system.

22. The computer-readable medium of claim 21, wherein the server system stores a referral request form.

23. The computer-readable medium of claim 21, wherein the server system stores a referral data form corresponding to the referral request form.

24. The computer-readable medium of claim 20, wherein the first provider comprises a health care provider.

25. The computer-readable medium of claim 20, wherein the first provider comprises the patient submitting the referral request to the first provider or the second provider.

26. The computer-readable medium of claim 20, wherein the second provider comprises a health care provider.

27. The computer-readable medium of claim 20, wherein accepting the referral request further comprises: monitoring the network by the second provider; submitting an acknowledgment of the referral request; placing the patient on a wait-list; providing an appointment for the patient; and examining the patient by the second provider.

28. The computer-readable medium of claim 20, wherein the medical record comprises medical history information for the patient, the medical history information comprising personal medical information, family information, and social information.

29. The computer-readable medium of claim 20, wherein importing and exporting the medical record comprises entering the medical history information manually.

30. The computer-readable medium of claim 20, wherein importing and exporting the medical record comprises hyperlinking the medical history information to the external system.

31. The computer-readable medium of claim 20, wherein importing and exporting the medical record comprises using an application programming interface.

32. The computer-readable medium of claim 20, wherein importing and exporting the medical record comprises using a paste and post method.

33. The computer-readable medium of claim 32, wherein the paste and post method further comprises: selecting the medical history information from an external system; copying the medical history information; pasting the medical history information into a clipboard;
matching the medical history information to a plurality of fields within the external system; and filling the plurality of fields with corresponding medical history information.

34. The computer-readable medium of claim 20, wherein the diagnostic information comprises: a summary report of an office examination of the patient; patient laboratory test results; and a list of medication prescribed by the second provider.

35. The computer-readable medium of claim 20, wherein the updated referral request is returned to the first provider.

36. The computer-readable medium of claim 20, wherein updating the status of the referral request is performed by the first provider or second provider.

37. The computer-readable medium of claim 20, wherein the status of the referral request comprises an indication of whether the patient has been seen by the second provider.

38. The computer-readable medium of claim 20, wherein the status is filtered and sorted according to a category.

39. An apparatus for electronically managing patient referrals, said apparatus comprising:
- in a network of interconnected computers, means for submitting a referral request from a first provider;
- means for accepting the referral request by a second provider;
- means for obtaining an insurance approval corresponding to the referral request;
- means for importing a medical record for a patient from a external system and
- means for exporting an updated medical record to the external system;
- means for receiving diagnostic information from the second provider, the diagnostic information being used to update the updated medical record; and
- means for updating a status of the referral request.

40. The apparatus of claim 39, wherein the network of interconnected computers comprises a server system.

41. The apparatus of claim 40 wherein the server system stores a referral request form.

42. The apparatus of claim 40 wherein the server system stores a referral data form corresponding to the referral request form.

43. The apparatus of claim 39, wherein the first provider comprises a health care provider.

44. The apparatus of claim 39, wherein the first provider comprises the patient submitting the referral request to the first provider or the second provider.

45. The apparatus of claim 39, wherein the means for accepting the referral request further comprises: monitoring the network by the second provider; submitting an acknowledgment of the referral request; placing the patient on a waitlist; providing an appointment for the patient; and examining the patient by the second provider.

46. The apparatus of claim 39, wherein the medical record comprises medical history information for the patient, the medical history information comprising personal medical information, family information, and social information.

47. The apparatus of claim 39, wherein the means for importing and the means for exporting the medical record comprises entering the medical history information manually.

48. The apparatus of claim 39, wherein the means for importing and the means for exporting the medical record comprises hyperlinking the medical history information to the external system.

49. The apparatus of claim 39, wherein the means for importing and the means for exporting the medical record comprises an application programming interface (API).

50. The apparatus of claim 39, wherein the means for importing and the means for exporting the medical record comprises a paste and post method.

51. The apparatus of claim of claim 50, wherein the paste and post method further comprises:
- selecting the medical history information from an external system;
- copying the medical history information;
- pasting the medical history information into a clipboard;
- matching the medical history information to a plurality of fields within the external system; and
- filling the plurality of fields with corresponding medical history information.

52. The apparatus of claim 39, wherein the diagnostic information comprises:
- a summary report of an office examination of the patient;
- patient laboratory test results; and
- a list of medication prescribed by the second provider.

53. The apparatus of claim 39, wherein the updated referral request is returned to the first provider.

54. The apparatus of claim 39, wherein the means for updating the status of the referral request is performed by the first provider or second provider.

55. The apparatus of claim 39, wherein the status of the referral request comprises an indication of whether the patient has been seen by the second provider.

56. The apparatus of claim 39, wherein the status is filtered and sorted according to a category.

57. The apparatus of claim 39, wherein the second provider comprises a health care provider.

* * * * *